US012796988B2

(12) United States Patent
Martinez et al.

(10) Patent No.: US 12,796,988 B2
(45) Date of Patent: Nov. 17, 2026

(54) DRY BIOPOTENTIAL ELECTRODE WITH PERFORATIONS

(71) Applicant: NANOLEQ AG, Rümlang (CH)

(72) Inventors: Vincent Martinez, Zurich (CH); Flurin Stauffer, Zurich (CH)

(73) Assignee: NANOLEQ AG, Rümlang (CH)

( * ) Notice: Subject to any disclaimer, the term of this patent is extended or adjusted under 35 U.S.C. 154(b) by 460 days.

(21) Appl. No.: 18/573,363

(22) PCT Filed: Jun. 28, 2022

(86) PCT No.: PCT/EP2022/067680
§ 371 (c)(1),
(2) Date: Dec. 21, 2023

(87) PCT Pub. No.: WO2023/275019
PCT Pub. Date: Jan. 5, 2023

(65) Prior Publication Data
US 2024/0285210 A1 Aug. 29, 2024

(30) Foreign Application Priority Data
Jun. 30, 2021 (EP) .................................... 21182862

(51) Int. Cl.
*A61B 5/259* (2021.01)
*A61B 5/00* (2006.01)
*A61B 5/265* (2021.01)
*A61B 5/27* (2021.01)

(52) U.S. Cl.
CPC .............. *A61B 5/259* (2021.01); *A61B 5/265* (2021.01); *A61B 5/27* (2021.01); *A61B 5/6804* (2013.01); *A61B 2560/0468* (2013.01); *A61B 2562/125* (2013.01); *A61B 2562/164* (2013.01); *A61B 2562/227* (2013.01)

(58) Field of Classification Search
CPC ........... A61B 5/259; A61B 5/27; A61B 5/265; A61B 5/6804; A61B 2560/0468; A61B 2562/125; A61B 2562/164; A61B 2562/227
See application file for complete search history.

(56) References Cited

U.S. PATENT DOCUMENTS 8,355,770 B2 1/2013 Chan et al.
2010/0292546 A1* 11/2010 Gonopolskiy ..... A61B 5/14552 600/310
(Continued)

FOREIGN PATENT DOCUMENTS

CN 106859637 A 6/2017
WO WO-2012066056 A1 * 5/2012 ........... A61B 5/6804
WO WO-2018004614 A1 * 1/2018 ............. A61B 5/263

OTHER PUBLICATIONS

International Search Report and Written Opinion for PCT Application No. PCT/EP2022/067680 mailed Oct. 6, 2022.
(Continued)

*Primary Examiner* — Adam Z Minchella
(74) *Attorney, Agent, or Firm* — Branch Partners PLLC; Bruce E. Black

(57) ABSTRACT

The present invention relates to a textile electrode, a textile product comprising a textile electrode and to a method of manufacturing a textile electrode.

18 Claims, 7 Drawing Sheets

(56) References Cited

U.S. PATENT DOCUMENTS

Figure 1:
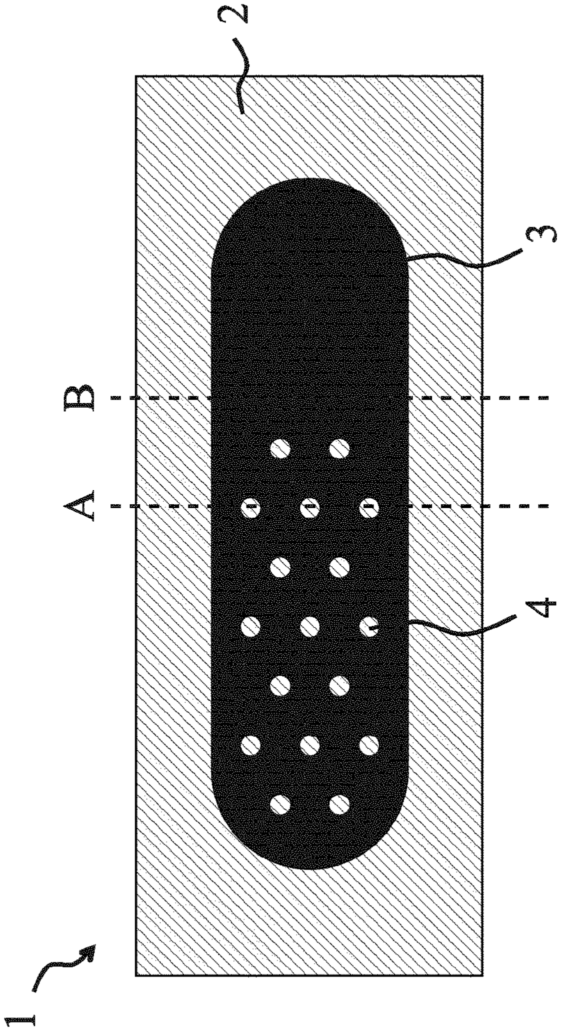

| | | | | |
|---|---|---|---|---|
| 2015/0359485 | A1* | 12/2015 | Berg | A61B 5/1118 600/388 |
| 2019/0231267 | A1* | 8/2019 | Oren | B32B 9/041 |
| 2020/0046246 | A1 | 2/2020 | Shu et al. | |
| 2023/0293076 | A1* | 9/2023 | Chen | A61B 5/259 600/391 |

OTHER PUBLICATIONS

International Preliminary Report on Patentability for PCT Application No. PCT/EP2022/067680 mailed Dec. 14, 2023.

Wu H, Yang G, Zhu K, Liu S, Guo W, Jiang Z, Li Z. Materials, Devices, and Systems of On-Skin Electrodes for Electrophysiological Monitoring and Human-Machine Interfaces. Adv Sci (Weinh). Dec. 4, 2020;8(2):2001938, 30 pages.

European Search Report for EP Patent Application No. 21182862.9 mailed Nov. 23, 2021.

* cited by examiner

DRY BIOPOTENTIAL ELECTRODE WITH PERFORATIONS

CROSS-REFERENCE TO RELATED APPLICATIONS

This present application is a U.S. national stage application of PCT Application No. PCT/EP2022/067680, filed Jun. 28, 2022, which claims priority to European Patent Application No. 21182862.9, filed Jun. 30, 2021, both of which are hereby incorporated by reference in their entirety.

The present invention relates to a textile electrode, a textile product comprising a textile electrode and to a method of manufacturing a textile electrode.

In recent years, health-monitoring textiles have become more and more important. Such health-monitoring textiles require certain textile sensors such as textile-integrated electrodes. To measure a high-quality biosignal with a textile-integrated electrode, a low and stable electrode-skin impedance is required. However, the skin conditions of a user may vary during use from extremely dry to soaked, e.g., due to sweat. This leads to a high variety of impedance levels spanning from e.g., 20 kΩ to more than 2 MΩ. Such high varieties can occur due to different skin types and skin treatments among different people on the one hand, and external influences such as air temperatures and air humidity on the other hand. For example, during low temperatures and low air humidity in winter the skin tends to be driest, causing a higher skin impedance when interfaced with dry electrodes. Moreover, movements at the electrode-skin interface can create impeding motion artifacts. The higher the impedance and the bigger the impedance changes, the bigger these artifacts. In addition, when the textile-integrated electrode is integrated in garments there is only a limited electrode-skin pressure applicable.

It is thus an object of the present invention to provide an improved textile electrode which allows measuring a high-quality biosignal by maintaining a low and stable electrode-skin impedance. This object is achieved with a textile electrode according to claim 1 (as well as the corresponding textile product and method of manufacturing the textile electrode). The dependent claims relate to preferred embodiments.

Accordingly, the present invention provides a textile electrode comprising a backing and a laminar electrode. The backing comprises, and preferably consists of, a textile material. The laminar electrode has first and second surfaces, the first surface being arranged and configured to be in direct contact with skin of a person during use and the second surface being (directly or indirectly) attached to the textile backing. The laminar electrode is electrically conductive and comprises through holes extending from the first surface to the second surface of the laminar electrode. The laminar electrode, at areas without any through holes, has a higher resistance to water penetration than the textile backing. At areas without any through holes, the laminar electrode has a resistance to water penetration that is preferably greater than 10 mBar.

The combination of the textile backing and the through holes in the laminar electrode provides two technical advantages. First and foremost, the through holes allow for electrode-skin wetting from outside of a textile product comprising the textile electrode when it is already being worn. This substantially reduces the electrode-skin impedance and the signal quality of the recorded signal during the first minutes of wear and improves the user experience as it is more convenient to wet the electrodes after the textile product has been put on by the user. When wetting the textile backing from outside, water can penetrate through the water-permeable textile backing as well as through the through holes of the laminar electrode and thus wet the skin of the user underneath the laminar electrode. In addition, wetting of an electrode may help to establish a low enough electrode-skin impedance faster than when relying on wetting of the electrode by sweat, i.e., the wetting may help to reduce the electrode settling time. Thus, it may be understood that the through holes are not sealed with and/or occluded by any material. In other words, the through holes are configured and/or capable of transporting water.

A second advantage of the textile electrode of the present invention will be apparent during long term use when sweat generated by the user underneath the electrode accumulates in the through holes and is drained by the textile backing. This can avoid skin irritations and lifting of the electrode from the skin. Accordingly, the adhesion of the electrodes to the skin is improved which ensures a stable electrode-skin interface and, hence, improved signal quality during movements of the user.

So far, no electrodes available in the prior art (a review of which may be found, e.g., in Hao Wu et al.: "Materials, Devices, and Systems of On-Skin Electrodes for Electrophysiological Monitoring and Human-Machine Interfaces", Advanced Science, vol. 8, 2, Jan. 20, 2021) provide the above-mentioned benefits. For example, conventional dry electrodes (described, for example, in U.S. Pat. No. 8,355,770 B2) are not wettable from outside, do not provide sweat drainage and can, thus, induce sweating between skin and electrode. Microporous, hydrophobic electrodes (described, for example, in CN 106859637) are also not wettable from the outside and do not drain any liquid sweat. Moreover, the contact surface area between the electrode and the skin is substantially reduced for such microporous electrodes. While electrodes that are microporous and hydrophilic (described, for example, in US 2020/0046246 A1) do drain sweat, the contact surface area between the electrode and the skin is substantially reduced which causes a worse contact impedance, especially in dry conditions. In general, decreasing the contact surface area between the electrode and the skin causes an increase in the electrode-skin impedance in dry conditions and lowers the skin adhesion, both potentially negatively impacting the biopotential signal quality, especially during movements of the user.

The resistance to water penetration may be measured according to ISO 811:2018 using a test speed of 60 cm water column per minute. Ideally, the resistance to water penetration should be measured for a test specimen having an area of 100 $cm^2$ as specified in ISO 8911:2018. However, as the resistance to water penetration of the electrode material should not take the effect of any through hole into account, the measurement may be performed with a circular section of the electrode having an area of 1 $cm^2$ which does not comprise a single through hole. Should such an area not be available, the through holes may be sealed with silicone sealant for silicone electrodes (such as silicone sealant Dow corning 734) or with respective sealants appropriate for the electrode materials (e.g. rubber or polyurethane sealants) before performing the measurement. The resistance to water penetration of the laminar electrode shall be greater than 10 mBar, preferably greater than 25 mBar and more preferably greater than 50 mBar.

By providing the electrode material, at areas without any through holes, with a resistance to water penetration that is greater than 10 mBar, capillary forces occurring in the through holes may be amplified. In this way, the transport of water to the person's skin may be improved.

Preferably, at least 50%, more preferably at least 75%, even more preferably at least 90%, even more preferably 100% of the first surface is arranged and configured to be in direct contact with skin of a person during use.

Preferably, the first surface arranged and configured to be in direct contact with the skin of a person during use is a continuous and/or smooth surface. In other words, it may be understood that the first surface does not comprise any steps, bumps, protrusions or the like. More preferably, the first surface is flat.

Preferably, the first surface of the laminar electrode, at areas without any through holes, has a higher water contact angle than the outer surface of the textile backing. Preferably, the water contact angle of the outer surface of the textile backing is smaller than 90°, more preferably smaller than 60° and most preferably smaller than 30°. It is particularly preferable that water is fully wetting the textile backing.

The water contact angle may be measured according to ASTMD 5725-99, wherein the contact angle is measured 10 seconds after initial contact between the water droplet and the respective surface.

The textile backing is preferably water permeable. Preferably, the volume of water that penetrates through the backing within 10 minutes amounts to at least 100 ml, more preferably to at least 250 ml and most preferably to at least 500 ml when exposed to water drops that amount to 800 ml of water in total. The water permeability may be measured according to ISO 9865:1991.

At areas without any through holes, the laminar electrode preferably has a water vapor transmission rate lower than 10,000 $g/m^2/d$, preferably lower than 5,000 $g/m^2/d$, most preferably lower than 2,000 $g/m^2/d$. The water vapor transmission rate may be measured according to JIS L 1099-B1.

The through holes may generally have any shape. However, cylindrical through holes with a circular cross-section are preferred. The cross-sectional area of each through hole is preferably greater than 0.4 $mm^2$, more preferably greater than 1 $mm^2$, and most preferably greater than 2 $mm^2$. The cross-sectional area of each through hole is preferably smaller than 50 $mm^2$, more preferably smaller than 30 $mm^2$ and most preferably smaller than 10 $mm^2$. If the cross-section varies along the thickness of the laminar electrode, these dimensions preferably apply to the cross-sectional area of the smallest cross-section.

The total cross-sectional area of all through holes preferably amounts to at least 3%, more preferably at least 5% and most preferably at least 7% of the area of the first surface of the electrode. Preferably, the total cross-sectional area of all through holes amounts to at most 30%, more preferably at most 20% and most preferably at most 10% of the area of the first surface of the electrode.

The cross-section of the through holes has a maximum dimension and the laminar electrode has a thickness. Preferably, the ratio of the maximum dimension to the thickness is greater than 1, more preferably greater than 2, even more preferably greater than 3 and most preferably greater than 4.

The through holes are preferably provided in a homogenous, more preferably a regular, pattern over the laminar electrode or over at least an area of the laminar electrode.

Preferably, the textile material of the backing has directional water transport properties with a preferred direction going from a surface of the textile backing facing away from the laminar electrode towards the surface of the textile backing attached to the second surface of the laminar electrode.

The electrical conductivity of the laminar electrode is preferably greater than 1 S/m, more preferably greater than 10 S/m and most preferably greater than 100 S/m.

The laminar electrode may consist of a single layer. It is, however, preferred that the laminar electrode comprises two or more layers. For example, the laminar electrode may comprise a conductive fabric attached to the textile backing and an additional conductive layer arranged to be in direct contact with skin of a person.

The conductive fabric preferably has an electrical conductivity of at least $10^2$ S/m, more preferably at least $10^3$ S/m and most preferably at least $10^4$ S/m. Furthermore, the conductive fabric preferably has a sheet resistance of less than 10 Ω/sq ("ohms per square"), more preferably less than 5 Ω/sq, most preferably less than 2 Ω/sq.

Preferably, the conductive fabric has a greater electrical conductivity than the additional conductive layer as the conductive fabric may be used to, e.g., provide electrical contact to an electrical connector being in electrical contact with the laminar electrode. The additional conductive layer preferably has an electrical conductivity of at least 0.1 S/m, more preferably at least 1 S/m and most preferably at least 10 S/m.

Preferably, the conductive layer is adhesive to skin. The adhesion to the skin is preferably higher than 0.1 $N/cm^2$, more preferably higher than 0.5 $N/cm^2$, most preferably higher than 1 $N/cm^2$. For this purpose, the conductive layer may, e.g., be silicone-based and may comprise carbon and/or silver. The conductive fabric may, e.g., be a fabric comprising silver. A particularly preferred conductive fabric is a fabric based on nylon coated with silver.

Preferably, the laminar electrode is attached to the textile backing by means of an adhesive layer. The adhesive layer may comprise one or a combination of the following materials: polyurethane, silicone.

Preferably, the conductive fabric and the conductive layer are attached to each other by means of an adhesive layer. The adhesive layer is preferably also conductive. The conductive layer may also be laminated or printed onto the conductive fabric.

The adhesive of the adhesive layer may penetrate at least a portion of the adjacent layers, i.e. at least a portion of the conductive fabric and/or the textile backing.

The adhesive layer between the laminar electrode and the textile backing preferably comprises perforations. The perforations preferably have a maximum cross-section between 0.2 $mm^2$ and 20 $mm^2$, preferably between 0.4 $mm^2$ and 8 $mm^2$, and most preferably between 0.7 $mm^2$ and 3.5 $mm^2$.

The textile electrode may further comprise a non-conducting ring surrounding the laminar electrode. The non-conducting ring may comprise various layers such as a textile layer, an adhesive layer and/or a layer based on, e.g., silicone or polyurethane. Preferably, the electrical conductivity of the non-conductive ring is smaller than $10^{-4}$ S/m, more preferably smaller than $10^{-7}$ S/m, and most preferably smaller than $10^{-10}$ S/m. Preferably, the non-conducting ring has anti-slip properties on human skin or even more preferably adhesion properties to the skin.

Preferably, the non-conducting ring is separated from the laminar electrode by means of a recess. This recess may have a similar effect as the through holes, i.e., the recess may also allow for wetting of the skin under the laminar electrode 3. It is thus preferred that the recess has a width between 0.3 mm and 4 mm, preferably between 0.5 mm and 2 mm, more preferably between 0.8 mm and 1.2 mm.

In order to collect the signals generated at the laminar electrode, the textile electrode preferably further comprises an electrical connector, which may be attached to an electrical wire. Preferably, one end of the electrical connector or the entire electrical connector is sandwiched between the backing and the laminar electrode so as to establish an electrical connection between the laminar electrode and the electrical connector. Preferably, the laminar electrode is attached to the backing by means of an adhesive layer, wherein the one end of the electrical connector is sandwiched between the backing of the adhesive layer of the laminar electrode. Preferably, the adhesive layer comprises perforations in an area sandwiched between the laminar electrode and the one end of the electrical connector so as to establish an electrical connection between the laminar electrode and the electrical connector.

The present invention further relates to a textile product comprising the textile electrode as described above. Preferably, the textile material of the backing of the electrode is an integral part of the textile of the textile product. In other words, the second surface of the laminar electrode is preferably directly attached to a textile layer of the textile product. The textile product may be any product that might benefit from an integrated electrode such as a T-shirt, a bra, a sport bra, undergarment, undershirt, a base layer, a sweatshirt, a shirt, a dress, underwear, a jacket, vest, a head band, a cap, pants, socks, swim wear, a swim suit, a diving suit, a bikini, compression garments, sport and medical bandages, a facemask, protective equipment, sports equipment, shoes, a helmet, headphones, gloves, sleeves, bracelets, watches, belts, a corset, a bodice, a one piece, a scarf.

The present invention further relates to a method of manufacturing the textile electrode as described above. The method comprises providing an electrically conductive laminar electrode with first and second surfaces, the first surface being arranged to be in direct contact with skin of a person, wherein the electrode material has a resistance to water penetration that is greater than 10 mBar. The method further comprises generating through holes in the laminar electrode extending from the first surface to the second surface of the laminar electrode. The method further comprises providing a textile backing, wherein the laminar electrode has a higher resistance to water penetration than the textile backing. Finally, the second surface of the laminar electrode is attached to the textile backing.

Of course, all features discussed above with regard to the textile electrode of the present invention may be employed analogously in the context of the method according to the present invention. This is, in particular, true for the material properties discussed above for the various layers of the textile electrode. However, in the context of the method the material properties may be measured for the materials before generating the through holes and before attaching the layers to each other.

Accordingly, it is preferred that the textile backing is water permeable, wherein the volume of water that penetrates through the textile backing (without the other components of the electrode being attached thereto) within 10 minutes preferably amounts to at least 100 ml, more preferably to at least 250 ml and most preferably to at least 500 ml when exposed to water drops that amount to 800 ml of water in total. It is further preferred that the laminar electrode, before generating the through holes, has a water vapor transmission rate lower than 10,000 $g/m^2/d$, preferably lower than 5,000 $g/m^2/d$, most preferably lower than 2,000 $g/m^2/d$.

Preferably, the first surface of the laminar electrode has a higher water contact angle than the surface of the textile backing which will not be attached to the laminar electrode.

Preferably, the step of providing an electrically conductive laminar electrode comprises providing a perforated adhesive layer, bonding the perforated adhesive layer to a conductive fabric and coating the conductive fabric with a, preferably adhesive, conductive layer.

As discussed above, the present invention allows the user to get liquid water through the textile backing onto the skin and therefore increases the skin humidity, which allows for improved electrode-skin contact and better biosignal recording quality. When the user wets the outer textile layer, it takes up the water. The textile backing is preferably selected so that it releases excessive water easily through the holes in the laminar electrode and this water remains in the holes and wets the skin. The combination of the above-discussed features allow the liquid water to prefer to stay on the skin rather than in the textile backing to improve the liquid transfer.

If water is applied onto the textile backing under pressure, the wet textile can bend down allowing the liquid to touch the skin. If the pressure is released, the textile withdraws. If the liquid prefers to stay on the textile, the liquid transfer is limited. The more hydrophobic the surface of the textile and the closer to the textile is approached to the skin that is hydrophobic, the easier water droplets stay on the skin.

Figure 1A:
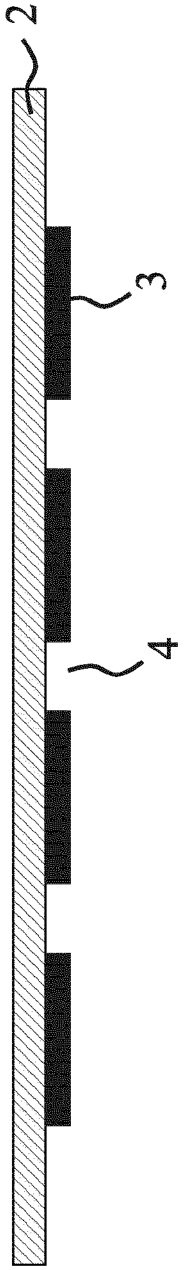
Figure 1B:
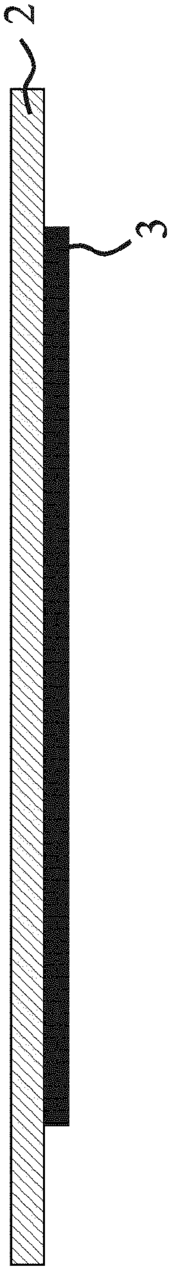
Figure 2A:
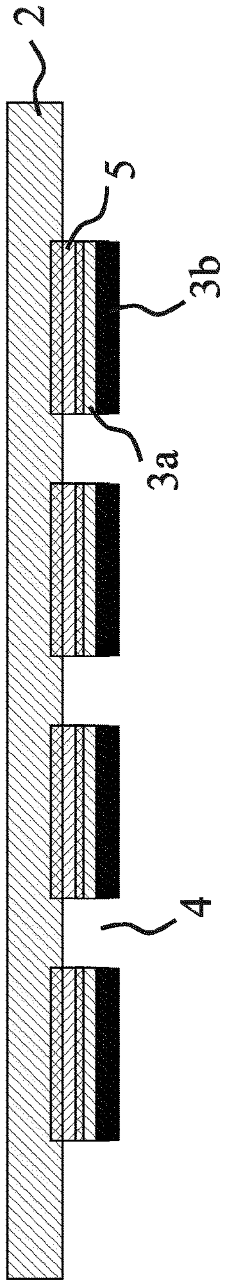
Figure 2B:
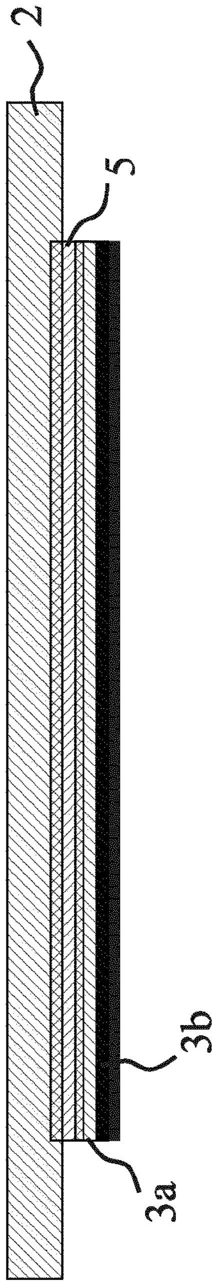
Figures 3, 3A, 3B, 4A, 4B:
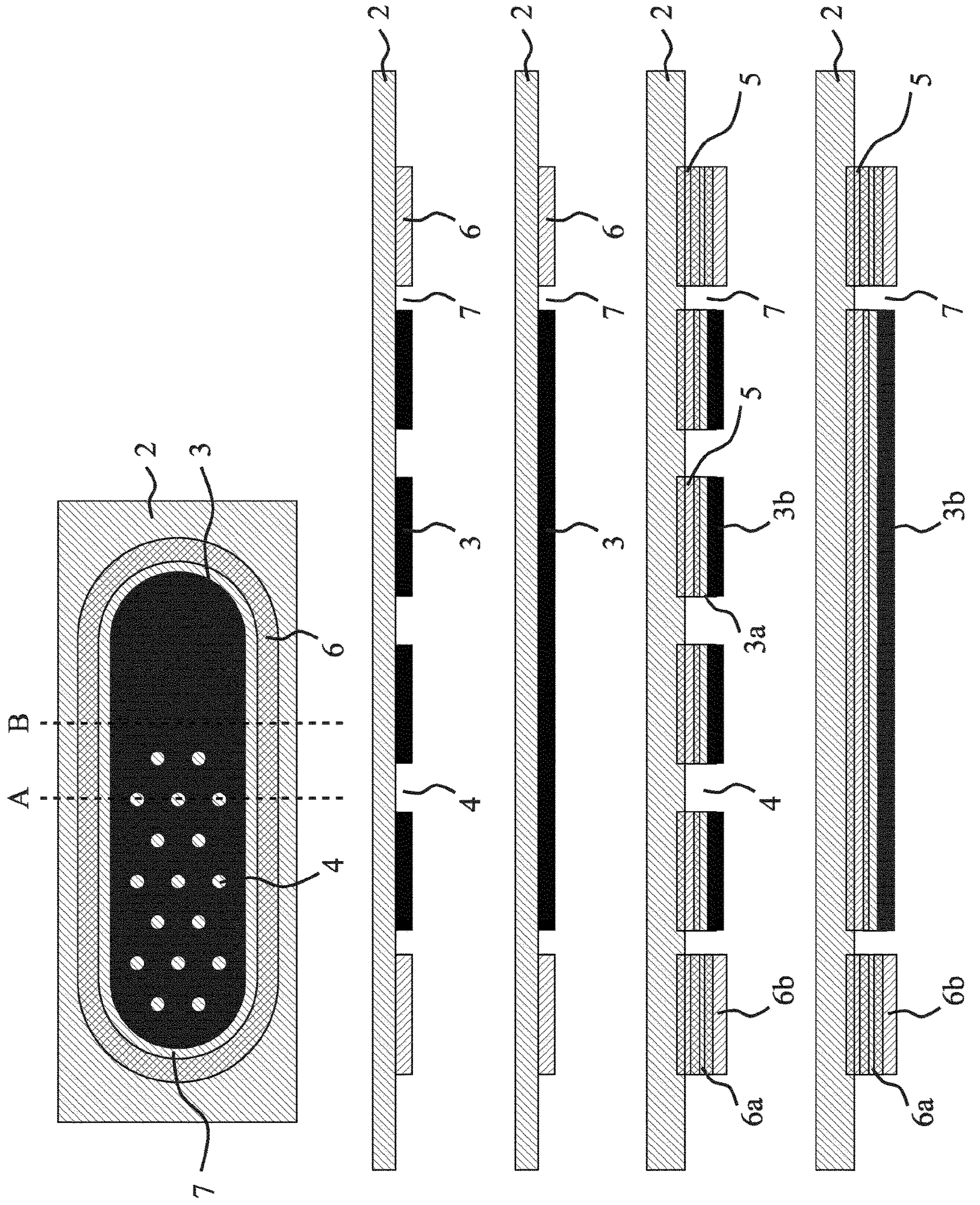
Figures 5, 5A, 5B, 5C:
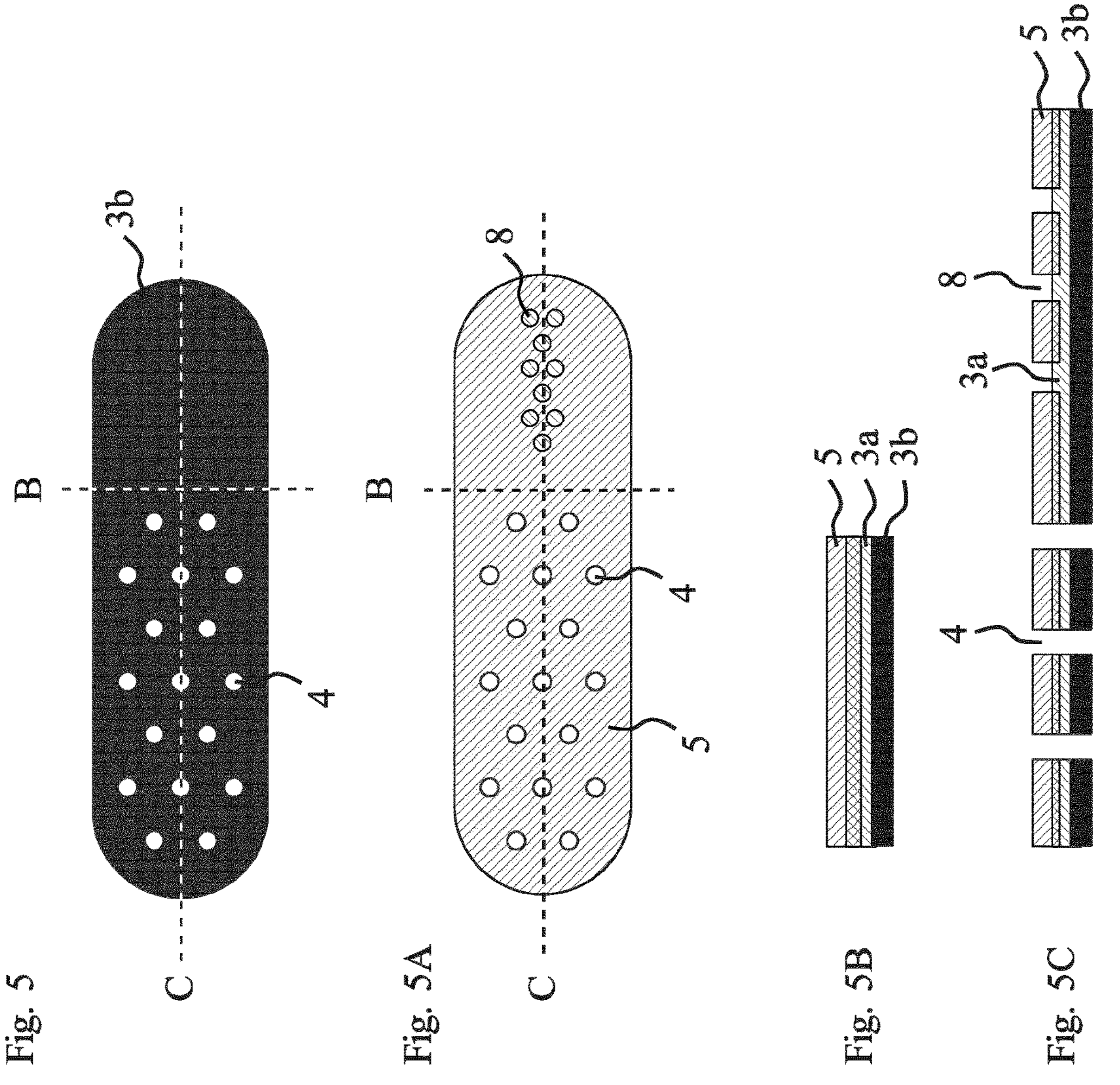
Figure 6:
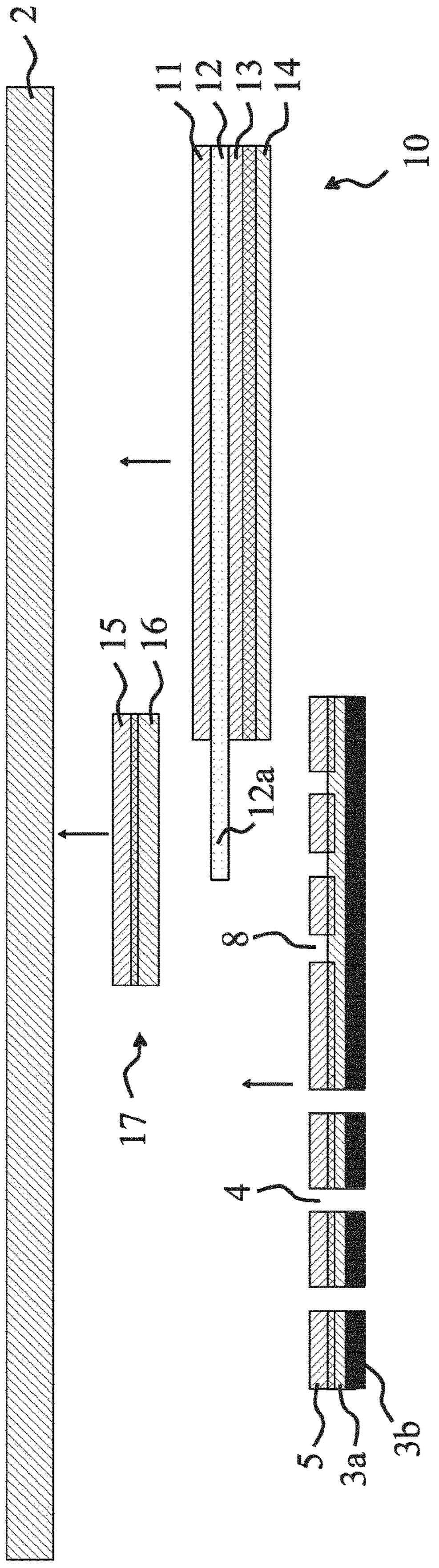
Figure 7:
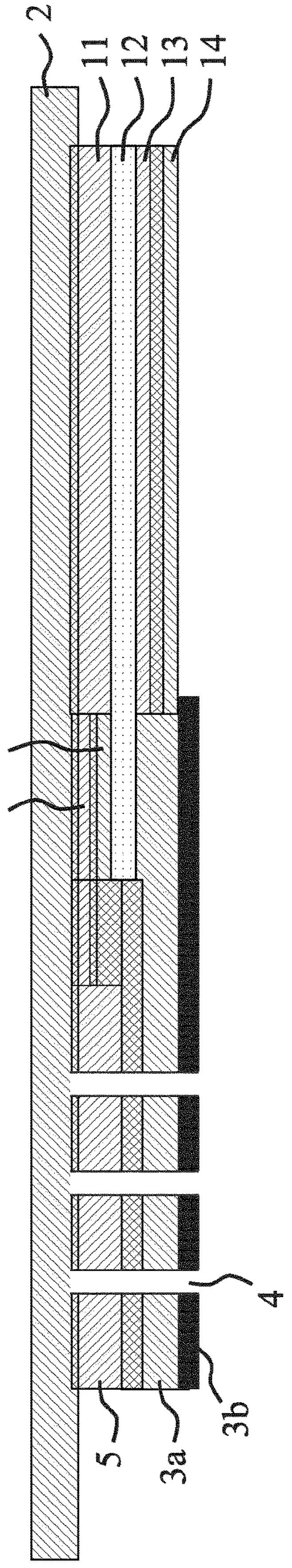
Figure 9:
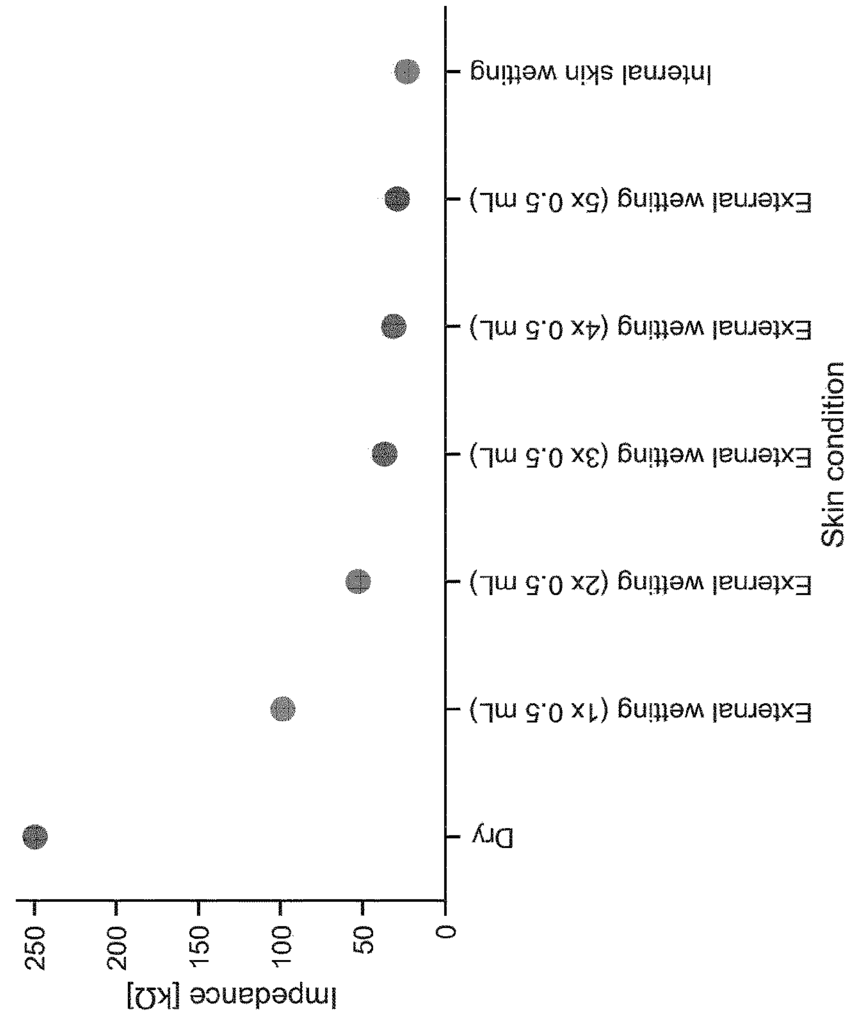
Figure 8:
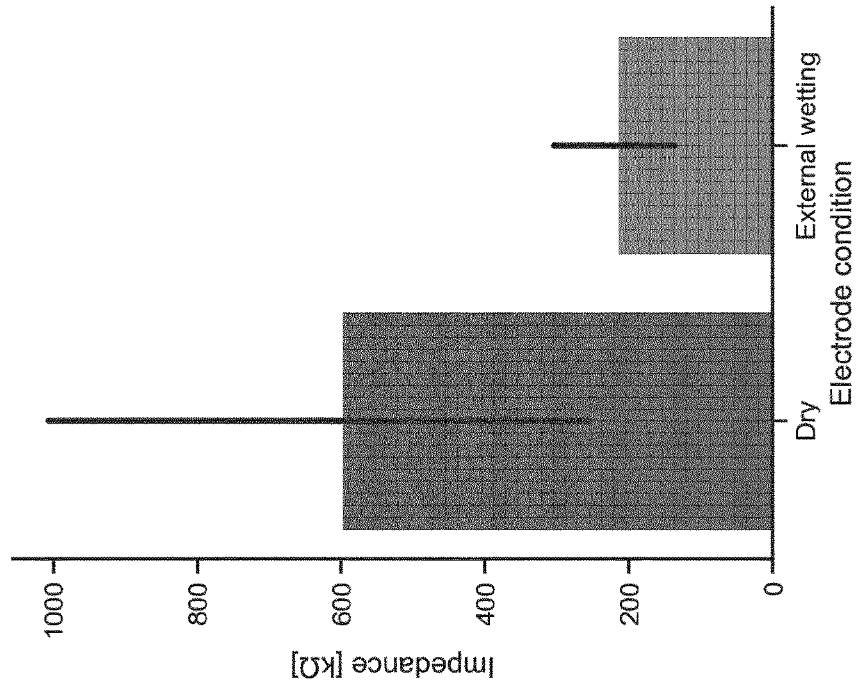
Figure 10:
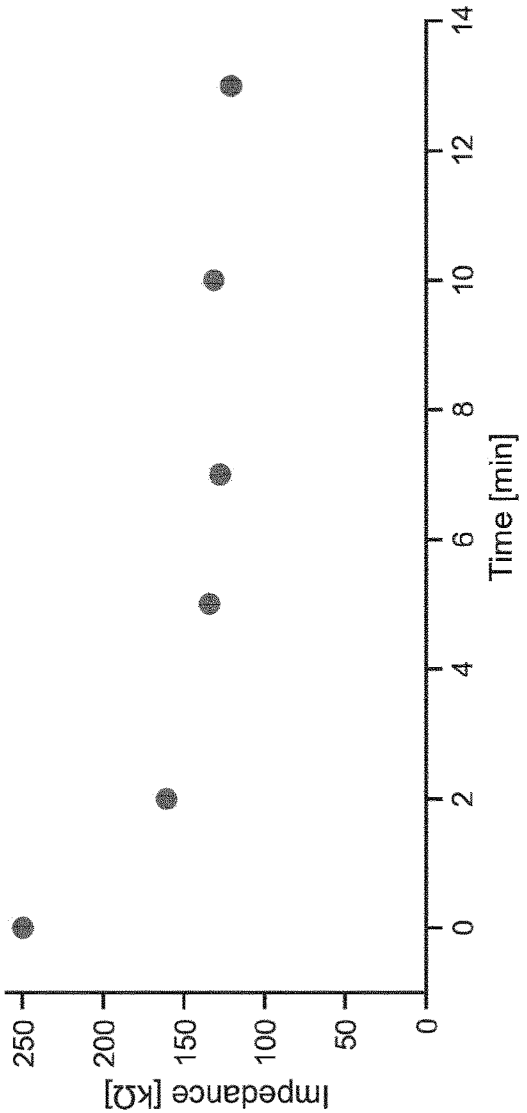
Figure 11:
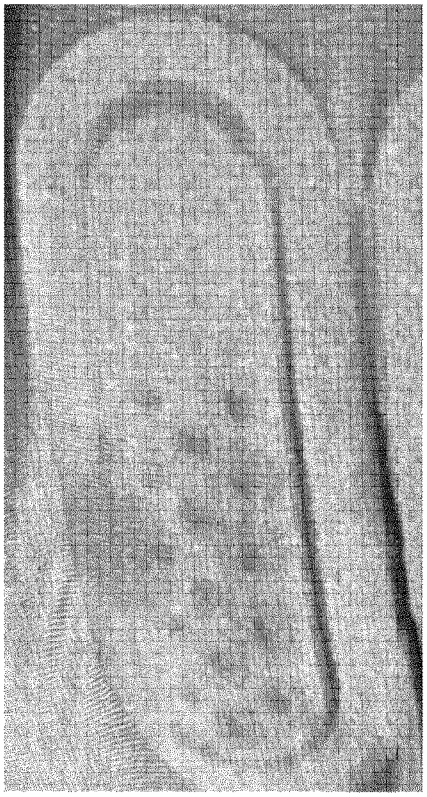

Preferred embodiments of the present invention will now be further elucidated with reference to the FIGURES which show:

FIG. 1: a bottom view of a preferred embodiment of a textile electrode according to the present invention;

FIG. 1A: a cross-section through the textile electrode of FIG. 1 along line A;

FIG. 1B: a cross-section through the textile electrode of FIG. 1 along line B;

FIG. 2A: a cross-section through a textile electrode according to another preferred embodiment of the present invention along line A of FIG. 1;

FIG. 2B: a cross-section through a textile electrode according to the embodiment of FIG. 2A along line B of FIG. 1;

FIG. 3: a bottom view of a preferred embodiment of a textile electrode according to the present invention;

FIG. 3A: a cross-section through the textile electrode of FIG. 3 along line A;

FIG. 3B: a cross-section through the textile electrode of FIG. 3 along line B;

FIG. 4A: a cross-section through a textile electrode according to another preferred embodiment of the present invention along line A of FIG. 3;

FIG. 4B: a cross-section through a textile electrode according to the embodiment of FIG. 4A along line B of FIG. 3;

FIG. 5: a bottom view of a laminar electrode of a textile electrode according to a preferred embodiment of the present invention;

FIG. 5A: a top view of the laminar electrode of FIG. 5;

FIG. 5B: a cross-section through the laminar electrode of FIG. 5 along line B;

FIG. 5C: a cross-section through the laminar electrode of FIG. 5 along line C;

FIG. 6: schematically a method of manufacturing a textile electrode with an electrical contact according a to preferred embodiment of the present invention;

FIG. 7: the assembled textile electrode with the electrical contact according to the embodiment of FIG. 6;

FIG. 8: the result of a measurement of electrode-skin impedance;

FIG. 9: the result of a measurement of electrode-skin impedance with repetitive external wetting;

FIG. 10: the result of a control measurement of electrode-skin impedance over time; and FIG. 11: a photograph of an exemplary textile product after intensive exercising.

FIG. 1 shows a bottom view of a textile electrode 1 according to a preferred embodiment of the present invention. The textile electrode 1 comprises a textile backing 2 and a laminar electrode 3 with a first surface (visible in FIG. 1) and a second surface attached to the textile backing 2. The first surface of the laminar electrode 3 is supposed to be arranged in direct contact with the skin of a person. The laminar electrode 3 is electrically conductive and comprises several through holes for extending from the first surface to the second surface of the laminar electrode (see the cross-section in FIG. 1A). As mentioned above, the laminar electrode of the present invention comprises a material which, at areas without any through holes 4, has a higher resistance to water penetration and a higher water contact angle than the material of the textile backing 2. At areas without any through holes 4, the laminar electrode 3 further has a resistance to water penetration that is greater than 10 mBar.

In the embodiment shown in FIG. 1, the textile backing 2 has a rectangular shape and the laminar electrode 3 has an oval shape. It will, however, be apparent to the skilled person that other shapes may be employed with different relative sizes as well. For example, the laminar electrode 3 may also be circular, elliptical, quadratic or rectangular in shape or may have any other irregular or regular shape suitable for an electrode. The textile backing 2 will, in many cases, be an integral part of a larger textile product such as a T-shirt. Accordingly, the actual shape of the textile backing 2 is of no relevance for the present invention.

The through holes 4 are shown to be cylindrical having a circular cross-section in FIGS. 1 and 1A. However, again other shapes are envisaged as well for the through holes 4 and may also be circular, elliptical, quadratic or rectangular in shape or may have any other irregular or regular shape. The through holes 4 should be arranged in a somewhat homogeneous or even regular pattern over the laminar electrode 3. In FIG. 1, a hexagonal pattern has been chosen to arrange the through holes 4 equidistantly.

While such an arrangement is preferable in terms of achieving a homogeneous effect, other arrangements of the through holes 4 are also possible. As shown in FIG. 1, the through holes 4 need not be spread out over the entire surface of the laminar electrode 3. Rather, a certain portion of the laminar electrode 3 may also be free of such through holes 4. The reasons therefor will be evident when discussing FIGS. 6 and 7 below.

The textile backing may comprise any textile material known for textile products and may comprise one or a combination of the following materials: elastane, polyamide, nylon, polyester, polyethylene, polyurethane, polypropylene, viscose. Preferably, the weight of the textile backing is less than 600 g/m$^2$, more preferably less than 400 g/m$^2$, most preferably less than 250 g/m$^2$ and/or the density of the textile backing is smaller than 1.5 g/cm$^3$, more preferably smaller than 1.1 g/cm$^3$, most preferably smaller than 0.8 g/cm$^3$.

The material of the laminar electrode is optimized to adapt to the skin of a user. Preferably, the material of the laminar electrode, at least at the first surface, is somewhat adhesive to human skin. Particularly preferable laminar electrodes are based on silicone and comprise carbon and/or silver in order to become conductive.

The laminar electrode 3 is attached to the textile backing 2 by, e.g., a suitable adhesive material. Moreover, the laminar electrode 3 may comprise several layers as shown in the embodiment of FIGS. 2A and 2B. In this embodiment, the laminar electrode 3 comprises a conductive fabric 3*a* and a further conductive layer 3*b*. The conductive fabric is preferably more conductive than the additional conductive layer and may, e.g., be a fabric comprising silver. Said conductive fabric 3*a* may be directly covered with the additional conductive layer 3*b*. For example, a carbon-silicone-based conductive layer 3*b* may be printed in liquid state onto the conductive fabric 3*a* and subsequently vulcanized. Alternatively, the conductive layer 3*b* may be directly laminated onto the conductive fabric 3*a*.

The entire laminar electrode 3 is preferably attached to the textile backing 2 by means of an adhesive layer 5. Suitable adhesive materials are the following: polyurethanes, silicones.

Since both the laminar electrode and the adhesive layer 5 may not be sufficiently water-permeable, it is preferred that the through holes 4 extend not only through the entire laminar electrode (i.e. from the first surface to the second surface), but also through the adhesive layer 5. In other words, it is preferred that the through holes 4 extend from the first surface of the laminar electrode all the way to the surface of the textile backing 2 as shown in FIG. 2A.

If the textile backing 2 is, for example, part of a T-shirt, said textile backing 2 may be wetted while the T-shirt is being worn by a user. The water then penetrates the textile backing 2, enters into the trough-holes 4 and thus wets the skin of the user being in contact with the first surface of the laminar electrode 3. Various experiments of the inventors (some of which are discussed further below) have shown that the impedance between the skin and the laminar electrode 3 is substantially reduced after wetting which improves the signal quality. The change of impedance may be caused by water simply wetting the bottom and, in particular, the edge of the hole, where the skin contacts the electrode. Moreover, the water may creep into the gap between the skin and the electrode adjacent to the hole. The more water one applies, the more the skin underneath the laminar electrodes is getting moist/wetted, eventually even reaching similar values as achieved by fully wetting the skin before applying the laminar electrode to the skin.

FIG. 3 shows a bottom view of another preferred embodiment of a textile electrode according to the present invention. Again, various cross-sections are shown in FIGS. 3A and 3B (with the laminar electrode 3 consisting of a single layer) and FIGS. 4A and 4B (with a multi-layered laminar electrode 3). In the embodiments shown in FIGS. 3-4B, the textile electrode further comprises a non-conducting ring 6 surrounding the laminar electrode 3. Similar to the laminar electrode 3, the non-conducting ring 6 may consist of a single layer such as non-conducting elastomers such silicone, polyurethane, rubber, or a textile fabric. Alternatively, the non-conducting ring 6 may comprise a non-conducting textile 6*a* and a non-conducting silicone layer 6*b* directly attached to each other by printing and subsequent vulcanizing, lamination or by means of an additional layer of adhesive. The entire non-conductive ring 6 may be attached to the textile backing 2 by means of a further layer of adhesive 5. In the embodiments shown in FIGS. 3-4B, the non-conductive ring 6 is separated from the laminar electrode 3 by means of a recess 7. This recess may have a similar effect as the through holes, i.e. the recess may also allow for wetting of the skin under the laminar electrode 3. It is thus preferred that the recess has a width between 0.3 mm and 4 mm, preferably between 0.5 mm and 2 mm, more preferably between 0.8 mm and 1.2 mm. The non-conductive ring 6 may, however, also be in direct contact with the laminar electrode 3.

As discussed in more detail below, the textile electrode of the present invention may comprise an electrical connector, wherein one end of the electrical connector is sandwiched between the textile backing 2 and the laminar electrode 3 so as to establish an electrical connection between the laminar electrode 3 and the electrical connector. Since the layer of adhesive 5, with which the laminar electrode 3 is attached to the textile backing 2, will typically be non-conductive, it is preferred to provide several perforations in an area of the adhesive layer 5 sandwiched between the laminar electrode 3 and the one end of the electrical connector so as to establish an electrical connection between the laminar electrode 3 and the electrical connector. A preferred embodiment of a laminar electrode 3 with such perforations 8 being present in the adhesive layer 5 is shown in FIGS. 5 to 5C. As is evident from FIGS. 5 and 5A, the laminar electrode 3 may be divided into two sections (here: left and right), wherein several through holes 4 are provided in one section (here: left), whereas the perforations 8 in the adhesive layer 5 are provided in the other section (here: right). Contrary to the through holes 4, which are preferably distributed homogeneously, the perforations 8 may be concentrated in a small stripe or other restricted area of the laminar electrode 3, which will, later on, come into contact with the electrical connector.

FIG. 7 shows a cross-section through a preferred embodiment of a textile electrode according to the present invention with an electrical connector. FIG. 6 schematically shows how the various components of the textile electrode shown in FIG. 7 are assembled.

When manufacturing the textile electrode of the present invention, the electrical conductive laminar electrode 3 with first and second surfaces is first provided or manufactured in the preferred example shown in FIG. 6, the adhesive layer 5 is first perforated with perforations 8. The perforated adhesive layer 5 is then bonded to the conductive fabric 3*a*, which is afterwards (or previously) coated with the additional conductive layer 3*b*.

Furthermore, an electrical contact patch 10 is prepared, which comprises an electrical contact or wire 12, adhesive layers 11 and 13 and the layer 14 of textile fabric or another suitable cover material. One end 12*a* of the electrical connector 12 protrudes from the electrical connector patch 10 so as to allow for establishing an electrical connection between the electrical connector 12 and the laminar electrode 3.

A further connection patch 17 comprises a layer of adhesive 15 and a layer of electrically conductive glue or fabric 16. In order to manufacture the textile electrode, said connection patch 17 is laminated onto the textile backing 2. Subsequently, the electrical connector patch 10 is laminated onto the textile backing 2 and the connection patch 17. Finally, the laminar electrode 3 is laminated onto the textile backing 2, the connection patch 17 and the electrical connector patch 10 so as to achieve the assembled product as shown in FIG. 7.

In the final product, electrical signals collected by the additional conductive layer 3*b* of the laminar electrode 3 are transmitted through the conductive fabric 3*a* of the laminar electrode 3 and through the perforations 8 of the adhesive layer 5 into the end 12*a* of the electrical connector 12. Wetting may take place on the left side of the laminar electrode 3 through the through holes 4 and through the recess 7 (in case there is a non-conductive ring). As is evident from FIG. 7, no through holes 4 are required on the right side of the laminar electrode 3, because wetting would be anyway blocked by the additional layers of the connection patch 17.

In order to show the beneficial effect of the textile electrode of the present invention, the following measurement has been performed.

The exemplary textile electrode used for the measurement had a composition as shown in FIGS. 4A and 4B and consisted of an adhesive carbon silicone layer 3*b*, conductive fabric (nylon, silver) 3*a*, a polyurethane adhesive layer 5 and a textile backing (71% polyester, 27% polyamide and 2% elastane) 2. The electrode had a length of 70 mm and a width of 20 mm with 15 through holes with a diameter of 3 mm and a non-conducting ring 6 made of an adhesive silicone 6*b*, a textile layer (72% polyamide, 28% elastane) 6*a* and a polyurethane adhesive layer 5 with a recess 7 of approximately 0.8 mm width. Two exemplary textile electrodes were incorporated into a T-Shirt made of 71% polyester, 27% polyamide and 2% elastane that acts as the textile backing layer 2. The electrodes were positioned below the chest muscle on the chest.

Seven different subjects were asked to wear the T-Shirt. Impedance between the skin of each subject and each of the textile electrodes of the T-Shirt was measured at a frequency of 10 Hz under dry conditions after 10 s wear time using a potentiostat capable of electrochemical impedance spectroscopy with a three-electrode setup. Commercial medical wet electrodes were placed on the forearm as counter and reference electrodes with the textile electrode as the working electrode. An average impedance of 600 kΩ was determined (see FIG. 8).

Subsequently, the T-Shirt was wetted from the outside by applying water by hand onto the T-Shirt. Impedance between the skin of each subject and each of the textile electrodes of the T-Shirt was again measured at a frequency of 10 Hz under wetted conditions after 10 s. An average impedance of 200 kΩ was determined (see FIG. 8).

In an additional experiment, the T-shirt was worn by a subject. One electrode was repetitively wetted from the outside by applying 0.5 mL of water with a Pasteur pipette, each time followed by an immediate impedance measurement. The initial dry impedance of 250 kΩ dropped to 99 kΩ after the first time external wetting, continued to decrease after each wetting repetition and reached an impedance value of 29 kΩ after 5 repeats (see FIG. 9). Finally, an impedance measurement was conducted after lifting the shirt, fully wetting the skin underneath and repressing the electrode on the shirt. The impedance value of the completely wet skin was 23 kΩ. As a control measurement, a second electrode in the same T-shirt was measured simultaneously over time without wetting. Sweating of the skin reduced the impedance to a value of 120 kΩ after a waiting time of 13 min (see FIG. 10). Wetting the electrode externally with 0.5 mL reduced the electrode-skin impedance immediately to a lower level than the control after a settling time of 13 min.

Accordingly, a substantial decrease in impedance could be achieved with the textile electrode of the present invention.

Each subject wearing the T-Shirt was then asked to perform extensive exercising in the form of running over 10 minutes. As may be taken from the photograph shown in FIG. 11, sweat generated during exercising under the electrodes could apparently penetrate the through holes and wet the outer side of the T-Shirt.

The invention claimed is:

1. A textile electrode comprising:
a backing comprising a textile material; and
a laminar electrode with first and second surfaces, the first surface being arranged to be in direct contact with skin of a person and the second surface being attached to the backing;
wherein the laminar electrode is electrically conductive and comprises through holes extending from the first surface to the second surface of the laminar electrode, wherein the laminar electrode comprises a material which, at areas without any through holes, has a higher resistance to water penetration than the textile material of the backing;
wherein the material of the laminar electrode, at areas without any through holes, has a resistance to water penetration that is greater than 10 mBar.

2. The textile electrode according to claim 1,
wherein the backing is water-permeable,
wherein a volume of water that penetrates through the backing within 10 minutes amounts to at least 100 mL when exposed to water drops that amount to 800 mL of water in total.

3. The textile electrode according to claim 1,
wherein a cross-sectional area of each through hole is greater than 0.4 $mm^2$ and/or wherein the cross-sectional area of each through hole is smaller than 50 $mm^2$.

4. The textile electrode according to claim 1,
wherein a total cross-sectional area of all through holes amounts to at least 3% of an area of the first surface of the laminar electrode and/or wherein the total cross-sectional area of all through holes amounts to at most 30% of the area of the first surface of the laminar electrode.

5. The textile electrode according to claim 1,
wherein a cross-section of the through holes has a maximum dimension, wherein the laminar electrode has a thickness and wherein a ratio of the maximum dimension to the thickness is greater than 1.

6. The textile electrode according to claim 1,
wherein the material of the laminar electrode, at areas without any through holes, has a water vapor transmission rate lower than 10,000 $g/m^2/d$.

7. The textile electrode according to claim 1,
wherein the first surface of the laminar electrode has a higher water contact angle than an outer surface of the backing.

8. The textile electrode according to claim 1,
wherein the laminar electrode is attached to the backing by means of an adhesive layer.

9. The textile electrode according to claim 1,
wherein the textile electrode further comprises an electrical connector, wherein one end of the electrical connector is sandwiched between the backing and the laminar electrode so as to establish an electrical connection between the laminar electrode and the electrical connector,
wherein the laminar electrode is attached to the backing by means of an adhesive layer and wherein the one end of the electrical connector is sandwiched between the backing and the adhesive layer of the laminar electrode.

10. A textile product comprising the textile electrode according to claim 1,
wherein the textile material of the backing of the textile electrode is an integral part of the textile of the textile product.

11. A method of manufacturing the textile electrode according to claim 1:
providing the laminar electrode;
generating the through holes in the laminar electrode extending from the first surface to the second surface of the laminar electrode;
providing the backing; and
attaching the second surface of the laminar electrode to the backing.

12. The method according to claim 11,
wherein the laminar electrode has a water vapor transmission rate lower than 10,000 $g/m^2/d$.

13. The method according to claim 11,
wherein the step of providing the laminar electrode comprises:
providing a perforated adhesive layer;
bonding the perforated adhesive layer to a conductive fabric; and
coating the conductive fabric with a conductive layer.

14. The textile electrode according to claim 8, wherein the adhesive layer comprises perforations.

15. The textile electrode according to claim 9, wherein the adhesive layer comprises perforations in an area sandwiched between the laminar electrode and the one end of the electrical connector so as to establish an electrical connection between the laminar electrode and the electrical connector.

16. The textile electrode according to claim 1,
wherein the textile electrode comprises a non-conducting ring.

17. The method according to claim 11,
wherein the backing is water-permeable, wherein a volume of water that penetrates through the textile backing within 10 minutes amounts to at least 100 mL when exposed to water drops that amount to 800 mL of water in total.

18. The method according to claim 13, wherein the conductive layer is an adhesive conductive layer.

* * * * *